US011717243B2

United States Patent
Ishii

(10) Patent No.: US 11,717,243 B2
(45) Date of Patent: Aug. 8, 2023

(54) MEDICAL INFORMATION PROCESSING APPARATUS, MEDICAL DIAGNOSTIC APPARATUS, MEDICAL INFORMATION PROCESSING SYSTEM, MEDICAL INFORMATION PROCESSING METHOD, MEDICAL IMAGING APPARATUS, AND MEDICAL TREATMENT APPARATUS

(71) Applicant: CANON MEDICAL SYSTEMS CORPORATION, Otawara (JP)

(72) Inventor: Takeshi Ishii, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 354 days.

(21) Appl. No.: 17/064,246

(22) Filed: Oct. 6, 2020

(65) Prior Publication Data
US 2021/0106303 A1 Apr. 15, 2021

(30) Foreign Application Priority Data
Oct. 9, 2019 (JP) .................................. 2019-186320

(51) Int. Cl.
*A61B 6/00* (2006.01)
*G06T 7/50* (2017.01)
(Continued)

(52) U.S. Cl.
CPC ............ *A61B 6/4441* (2013.01); *A61B 6/547* (2013.01); *G06T 7/50* (2017.01); *G06T 7/70* (2017.01);
(Continued)

(58) Field of Classification Search
None
See application file for complete search history.

(56) References Cited

U.S. PATENT DOCUMENTS

| 6,272,368 B1 | 8/2001 | Alexandrescu |
| 2013/0083894 A1* | 4/2013 | Niebler .................. A61B 6/547 378/62 |
| 2016/0074000 A1 | 3/2016 | Uehara et al. |

FOREIGN PATENT DOCUMENTS

| JP | 11-178818 A | 7/1999 |
| JP | 2009-022602 A | 2/2009 |

(Continued)

OTHER PUBLICATIONS

Girshick et al., "Rich Feature Hierarchies for Accurate Object Detection and Semantic Segmentation", arXiv:1311.2524v5 [cs.CV] Oct. 22, 2014, 20 Pages.

(Continued)

*Primary Examiner* — Hoon K Song
(74) *Attorney, Agent, or Firm* — Oblon, McClelland, Maier & Neustadt, L.L.P.

(57) ABSTRACT

A medical information processing apparatus according to an embodiment includes a processor. The processor acquires an examination room image obtained by capturing the inside of an examination room in which a medical imaging apparatus including a movement mechanism is installed. The processor specifies identification information of a target object depicted in the examination room image using the examination room image. The processor specifies three-dimensional shape data corresponding to the identification information of the target object using the identification information of the target object. The processor specifies the position of the three-dimensional shape data in a virtual three-dimensional space using depth information indicating distance from an examination-room image capturing device to the target object depicted in the examination room image.

20 Claims, 9 Drawing Sheets

(51) Int. Cl.
  *G06T 7/70*   (2017.01)
  *G06T 19/20*  (2011.01)
  *G06V 20/00*  (2022.01)
  *G06V 20/64*  (2022.01)

(52) U.S. Cl.
  CPC .............. *G06T 19/20* (2013.01); *G06V 20/00* (2022.01); *G06V 20/64* (2022.01); *G06T 2207/20081* (2013.01); *G06T 2210/41* (2013.01); *G06T 2219/2016* (2013.01); *G06V 2201/03* (2022.01)

(56) References Cited

FOREIGN PATENT DOCUMENTS

| JP | 2014-176495 A | 9/2014 |
|----|---------------|--------|
| JP | 2015-6333 A   | 1/2015 |

OTHER PUBLICATIONS

He et al., "Mask R-CNN", arXiv:1703.06870v3 [cs.CV] Jan. 24, 2018, 12 Pages.
Qi et al., "PointNet: Deep Learning on Point Sets for 3D Classification and Segmentation", arXiv:1612.00593v2 [cs.CV] Apr. 10, 2017, 19 Pages.
Japanese Office Action dated Apr. 18, 2023, issued in Japanese Application 2019-186320.

\* cited by examiner

| NAME OF TARGET OBJECT | THREE-DIMENSIONAL SHAPE DATA | EVASIVE REGION | EVASIVE ACTION |
|---|---|---|---|
| DEVICE A | ... | FIRST EVASIVE REGION | DECELERATION |
| | | SECOND EVASIVE REGION | STOP |
| DEVICE B | ... | FIRST EVASIVE REGION | DECELERATION |
| | | SECOND EVASIVE REGION | STOP |
| ... | ... | ... | ... |

MEDICAL INFORMATION PROCESSING APPARATUS, MEDICAL DIAGNOSTIC APPARATUS, MEDICAL INFORMATION PROCESSING SYSTEM, MEDICAL INFORMATION PROCESSING METHOD, MEDICAL IMAGING APPARATUS, AND MEDICAL TREATMENT APPARATUS

CROSS-REFERENCE TO RELATED APPLICATIONS

This application is based upon and claims the benefit of priority from Japanese Patent Application No. 2019-186320, filed on Oct. 9, 2019; the entire contents of which are incorporated herein by reference.

FIELD

Embodiments described herein relate generally to a medical information processing apparatus, a medical diagnostic apparatus, a medical information processing system, a medical information processing method, a medical imaging apparatus, and a medical treatment apparatus.

BACKGROUND

Conventionally, a medical imaging apparatus such as an X-ray Angio apparatus including a movable C arm and a movable table has been used in image capturing of the circulatory system such as a blood vessel or the heart. In a known technology of such a medical imaging apparatus, position information of units such as the C arm and the table included in the medical imaging apparatus is managed to perform control to evade contact of the units.

In another known technology, an instrument or a worker positioned around the medical imaging apparatus is detected using an image obtained by capturing the inside of an examination room by a camera, and the C arm, the table, or the like is prevented from contacting the detected instrument or worker. However, in the conventional technologies, the stereoscopic shape of any evasive target object depicted in a captured image has been specified by matching the outer shape of the evasive target object with a stereoscopic shape model stored in advance. Such shape-to-shape matching processing has taken processing time in some cases.

DETAILED DESCRIPTION

Embodiments of a medical information processing apparatus, a medical diagnostic apparatus, a medical information processing system, a medical information processing method, a medical imaging apparatus, and a medical treatment apparatus will be described below in detail with reference to the accompanying drawings.

First Embodiment

A medical information processing apparatus according to an embodiment includes a processor. The processor acquires an examination room image obtained by capturing the inside of an examination room in which a medical imaging apparatus including a movement mechanism is installed. The processor specifies identification information of a target object depicted in the examination room image using the examination room image. The processor specifies three-dimensional shape data corresponding to the identification information of the target object using the identification information of the target object. The processor specifies the position of the three-dimensional shape data in a virtual three-dimensional space representing a space in the examination room using depth information indicating the distance from an examination-room image capturing device having captured the examination room image to the target object depicted in the examination room image.

Figure 1:
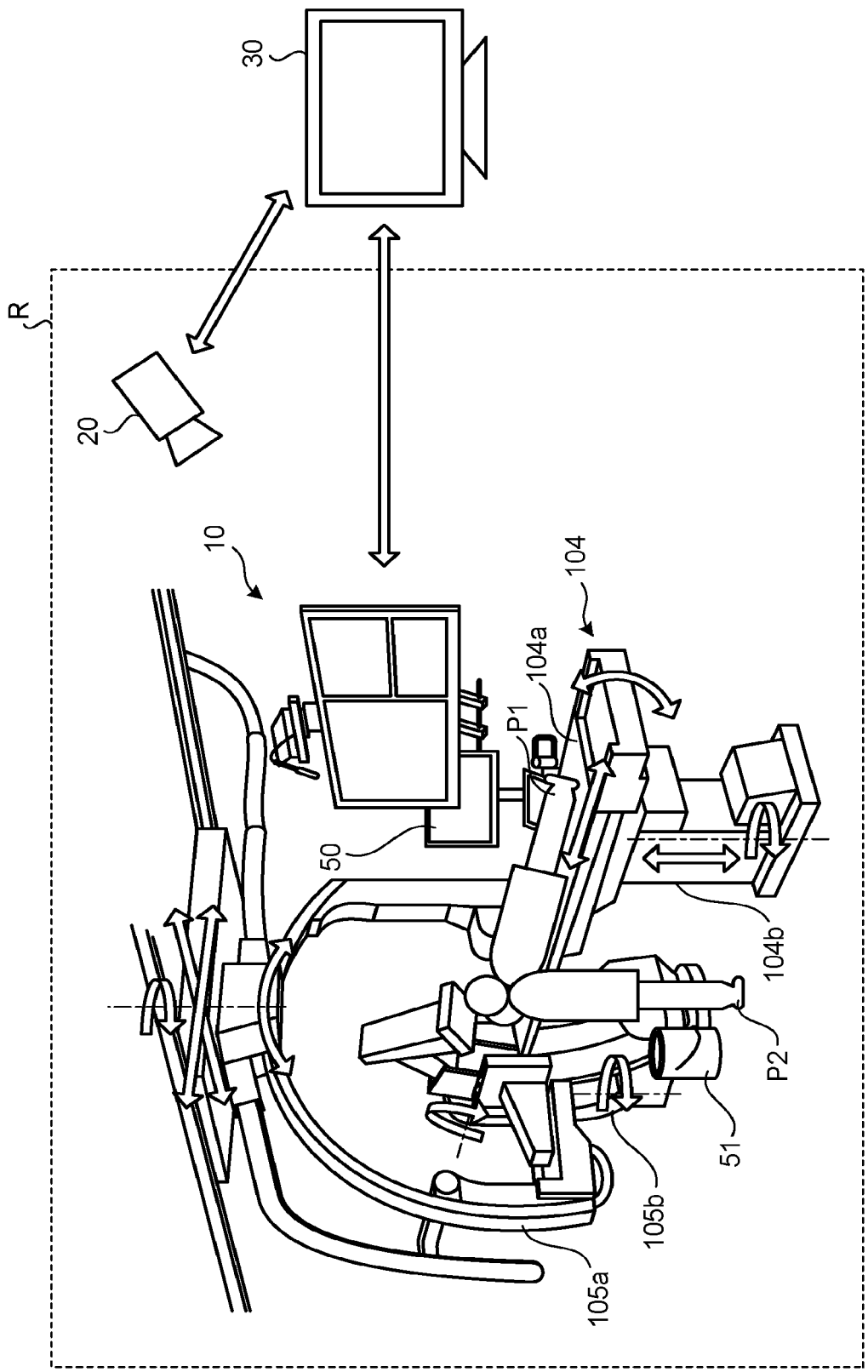
FIG. 1 is a diagram illustrating exemplary appearance of an examination room in which a medical imaging apparatus according to a first embodiment is installed.

FIG. 1 is a diagram illustrating an exemplary examination room R in which an X-ray diagnostic apparatus 10 according to the present embodiment is installed. As illustrated in FIG. 1, the X-ray diagnostic apparatus 10 includes C arms 105a and 105b (hereinafter simply referred to as C arms 105 when not distinguished from each other) holding an X-ray tube, an X-ray detector, and the like, and a table 104. The C arms 105 and the table 104 are movable units and are exemplary movement mechanisms in the present embodiment. The movement mechanisms include at least one of the C arms 105 or the table 104.

The C arms 105 and the table 104 can perform movement in an up-down direction, movement in a right-left direction (vertical direction), tilt, and rotation under control of a C-arm-table control circuitry to be described later. In the present embodiment, movement in the up-down direction, movement in the right-left direction (vertical direction), tilt, and rotation are collectively referred to as "movement" in some cases. The C arm 105a and the C arm 105b are separately movable. The table 104 includes a tabletop 104a on which a subject P1 is placed and a base 104b supporting the tabletop 104a. The tabletop 104a and the base 104b may be both movable or only the tabletop 104a may be movable.

The X-ray diagnostic apparatus 10 is an exemplary medical imaging apparatus in the present embodiment. The X-ray diagnostic apparatus 10 is also an exemplary medical diagnostic apparatus.

FIG. 1 illustrates an exemplary biplane configuration in which the X-ray diagnostic apparatus 10 includes the two C arms 105, but the X-ray diagnostic apparatus 10 may have a single-plane configuration including a single C arm 105. The C arm 105a suspended from the ceiling is referred to as a S (omega) arm.

An object or a person other than the X-ray diagnostic apparatus 10 exists in the examination room R. For example, an operator P2 such as a doctor or an engineer who operates the X-ray diagnostic apparatus 10, an ultrasonic wave diagnostic apparatus 50, and a bucket 51 exists in the examination room R in the example illustrated in FIG. 1. In the present embodiment, an object or a person other than the X-ray diagnostic apparatus 10 that exists in the examination room R is referred to as a target object or an evasive target object.

A target object is an object or a person that is likely to be an obstacle to movement of the movement mechanisms such as the C arms 105 and the table 104, but is not a body that is not an obstacle to movement of the movement mechanism. Such a body that is not an obstacle to movement of the movement mechanism is, for example, a poster or a calendar fixed to the wall of the examination room, but is not limited thereto.

The subject P1, the operator P2, the ultrasonic wave diagnostic apparatus 50, and the bucket 51 illustrated in FIG. 1 are not included in the X-ray diagnostic apparatus 10. A plurality of operators P2 may exist in the examination room R.

A stereo camera 20 is installed in the examination room R. The stereo camera 20 captures an image of the inside of the examination room R. The stereo camera 20 is an exemplary examination-room image capturing device in the present embodiment.

The image of the inside of the examination room R, which is captured by the stereo camera 20 is an exemplary examination room image in the present embodiment. For example, the stereo camera 20 simultaneously captures two examination room images having parallax therebetween through two lenses.

The stereo camera 20 transmits a captured examination room image to a medical information processing apparatus 30 through a network.

The medical information processing apparatus 30 is, for example, a server device or a personal computer (PC) installed in a hospital. The medical information processing apparatus 30 is installed outside the examination room R in FIG. 1 but may be installed inside the examination room R.

Figure 2:
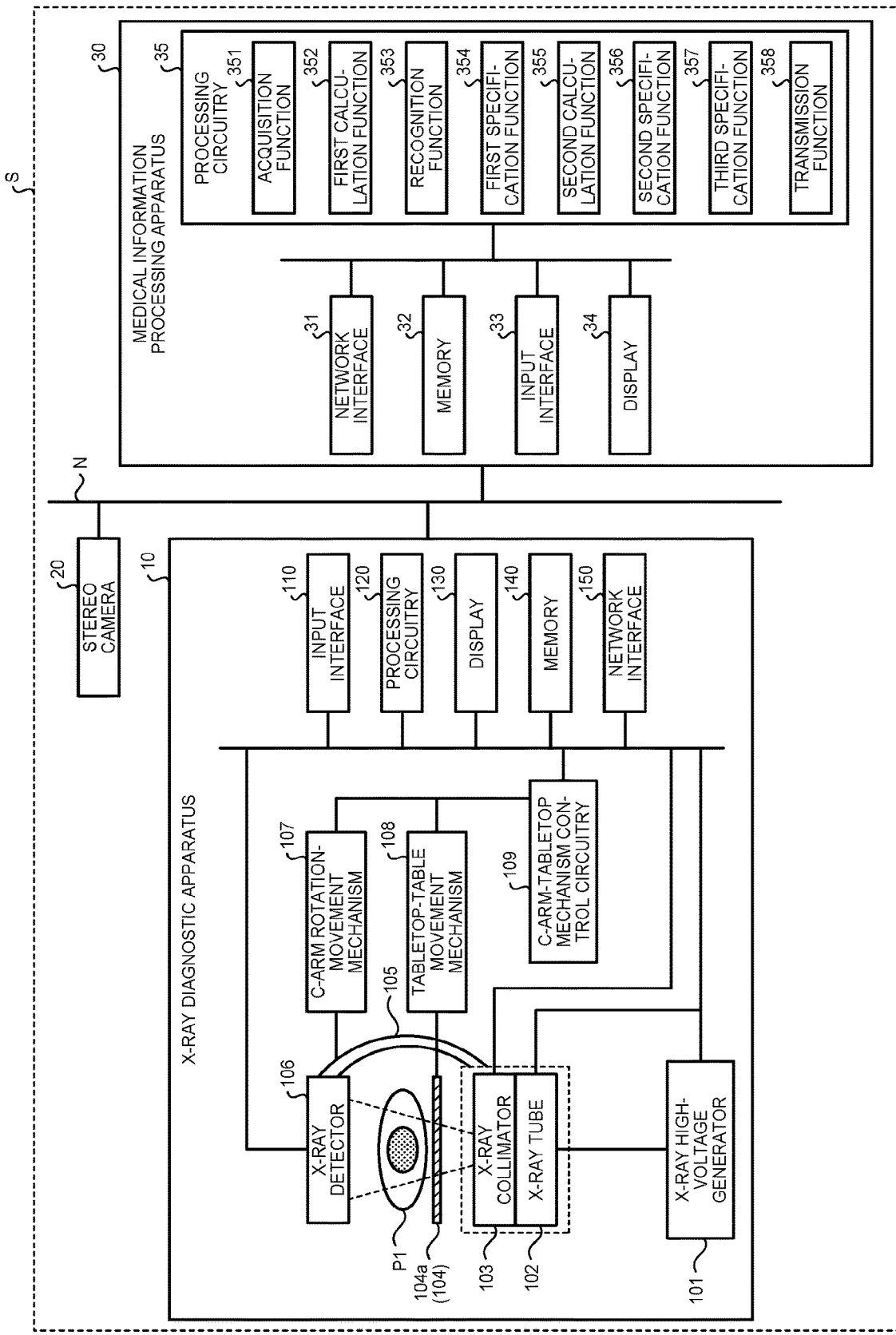
FIG. 2 is a block diagram illustrating an exemplary entire configuration of a medical information processing system according to the first embodiment.

The following describes a medical information processing system according to the present embodiment with reference to FIG. 2.

FIG. 2 is a block diagram illustrating an exemplary entire configuration of a medical information processing system S according to the present embodiment. As illustrated in FIG. 2, the medical information processing system S includes the X-ray diagnostic apparatus 10, the stereo camera 20, and the medical information processing apparatus 30. The medical information processing system S may include no stereo camera 20. The X-ray diagnostic apparatus 10, the stereo camera 20, and the medical information processing apparatus 30 are connected with one another through a network N such as an in-hospital local area network (LAN) installed in the hospital.

The X-ray diagnostic apparatus 10 includes an X-ray high-voltage generator 101, an X-ray tube 102, an X-ray collimator 103, the table 104 (including the tabletop 104a and the base 104b), the C arms 105, an X-ray detector 106, a C-arm rotation-movement mechanism 107, a tabletop-table movement mechanism 108, a C-arm-tabletop mechanism control circuitry 109, a processing circuitry 120, an input interface 110, a display 130, a memory 140, and a network interface 150. The base 104b of the table 104 is omitted in FIG. 2. One of the two C arms 105 is omitted in FIG. 2. Image capturing apparatus of the present embodiment includes at least of the X-ray high-voltage generator 101, the X-ray tube 102, the X-ray collimator 103, the C arms 105, the X-ray detector 106, the table 104, the C-arm rotation-movement mechanism 107, the tabletop-table movement mechanism 108, or the C-arm-tabletop mechanism control circuitry 109.

The X-ray high-voltage generator 101 is a high-voltage power source configured to generate high voltage and supply the generated high voltage to the X-ray tube 102.

The X-ray tube 102 generates an X-ray with the high voltage supplied from the X-ray high-voltage generator 101. The X-ray collimator 103 narrows the X-ray generated by the X-ray tube 102 so that the X-ray is selectively exposed in a region of interest (ROI) of the subject P1. The X-ray detector 106 detects the X-ray having transmitted through a subject P1 and transmits a result of the detection to the processing circuitry 120.

The C arms 105 hold the X-ray tube 102, the X-ray collimator 103, and the X-ray detector 106. The C arms 105 are moved in the up-down and right-left directions and rotated by the C-arm rotation-movement mechanism 107.

The C-arm rotation-movement mechanism 107 is a drive mechanism configured to move the C arms 105 and includes a motor, an actuator, and the like. The C-arm rotation-movement mechanism 107 moves the C arms 105 under control of the C-arm-tabletop mechanism control circuitry 109.

The table 104 includes the tabletop 104a and the base 104b. The tabletop 104a is a bed on which the subject P1 is placed, and is disposed on the base 104b. The tabletop 104a can be moved in the up-down direction or the horizontal direction and tilted. The base 104b can be moved in the up-down and right-left directions and rotated.

The tabletop-table movement mechanism 108 is a drive mechanism configured to move the tabletop 104a on which the subject P1 is placed in the horizontal and up-down directions under control of the C-arm-tabletop mechanism control circuitry 109, and includes a motor, an actuator, and the like. The tabletop-table movement mechanism 108 moves the base 104b in the horizontal and up-down directions. The tabletop-table movement mechanism 108 is installed, for example, inside the base 104b. The tabletop-table movement mechanism 108 includes a sensor configured to detect the positions of the tabletop 104a and the base 104b. The tabletop-table movement mechanism 108 sends the detected positions to the C-arm-tabletop mechanism control circuitry 109.

The C-arm-tabletop mechanism control circuitry 109 moves the C arms 105, the tabletop 104a, or the base 104b by controlling the C-arm rotation-movement mechanism 107 and the tabletop-table movement mechanism 108 under control of the processing circuitry 120. The C-arm-tabletop mechanism control circuitry 109 acquires the positions of the tabletop 104a and the base 104b from the tabletop-table movement mechanism 108 and transmits the positions to the processing circuitry 120. The C-arm-tabletop mechanism control circuitry 109 is, for example, a processor configured to read and execute a computer program stored in the memory 140 to be described later. The tabletop-table movement mechanism 108 may be separated to a C-arm control circuitry and a tabletop mechanism control circuitry.

The input interface 110 receives various input operations from an operator, converts the received input operations into electric signals, and outputs the electric signals to the processing circuitry 120. The input interface 110 is achieved by, for example, a mouse, a keyboard, a truck ball, a switch, a button, a joystick, a touch pad on which an input operation is performed through touch on an operation surface, a touch screen as integration of a display screen and a touch pad, a non-contact input circuitry including an optical sensor, a voice input circuitry, and a foot switch for performing X-ray irradiation or the like.

The input interface 110 may include a tablet terminal or the like capable of performing wireless communication with the X-ray diagnostic apparatus 10. The input interface 110 does not necessarily need to include a physical operation member such as a mouse or a keyboard. Examples of the input interface 110 include an electric signal processing circuitry that receives an electric signal corresponding to an input operation from an external input instrument provided separately from the X-ray diagnostic apparatus 10 and outputs the electric signal to the processing circuitry 120.

The display 130 is a liquid crystal display, a cathode ray tube (CRT) display, or the like and displays various kinds of information. The display 130 displays, for example, a graphical user interface (GUI) for receiving various instructions, various settings, and the like from the operator P2 through an input interface 33. The display 130 may be a desktop type or, for example, a tablet terminal capable of performing wireless communication with the X-ray diagnostic apparatus 10.

The memory 140 is achieved by a semiconductor memory element such as a random access memory (RAM) or a flash memory, a hard disk, an optical disk, or the like. For example, the memory 140 stores a computer program to be executed at a circuitry included in the X-ray diagnostic apparatus 10.

The network interface 150 is connected with the processing circuitry 120 and controls various kinds of data transmission and communication performed with the medical information processing apparatus 30 connected through the network N. The network interface 150 is achieved by a network card, a network adapter, a network interface controller (NIC), or the like. The memory 140 may be achieved by a cloud.

The processing circuitry 120 controls the entire X-ray diagnostic apparatus 10 to execute image capturing processing of capturing an image of the subject P1. The processing circuitry 120 receives (acquires) the position and orientation of three-dimensional shape data representing a target object in a virtual three-dimensional space representing the examination room R, which is transmitted from the medical information processing apparatus 30 through the network interface 150, and an evasive region and an evasive action that are associated with the three-dimensional shape data. The processing circuitry 120 controls movement of the movement mechanisms using these pieces of information transmitted from the medical information processing apparatus 30 so that the movement mechanisms evade the target object.

For example, using the information transmitted from the medical information processing apparatus 30, the processing circuitry 120 instructs, to the C-arm-tabletop mechanism control circuitry 109, a position, an angle, and a moving speed for moving the C arm 105, the tabletop 104a, or the base 104b. In addition, using the information transmitted from the medical information processing apparatus 30, the processing circuitry 120 instructs, to the C-arm-tabletop mechanism control circuitry 109, stopping of movement of the C arm 105, the tabletop 104a, or the base 104b. These controls may be executed by the C-arm-tabletop mechanism control circuitry 109.

The position and orientation of the three-dimensional shape data in the virtual three-dimensional space, which is transmitted from the medical information processing apparatus 30, and an evasive region and an evasive action associated with the three-dimensional shape data will be described later in detail.

The processing circuitry 120 is, for example, a processor configured to read and execute a computer program stored in the memory 140. The processing circuitry 120 is an exemplary controller in the present embodiment. Alternatively, the C-arm-tabletop mechanism control circuitry 109 may be an exemplary controller in the present embodiment. Alternatively, both the processing circuitry 120 and the C-arm-tabletop mechanism control circuitry 109 may be an exemplary controller.

The medical information processing apparatus 30 includes a network (NW) interface 31, a memory 32, the input interface 33, a display 34, and a processing circuitry 35.

The network interface 31 is connected with the processing circuitry 120 and controls various kinds of data transmission and communication performed with the X-ray diagnostic apparatus 10 or the stereo camera 20 connected through the network N.

The memory 32 is achieved by a semiconductor memory element such as a RAM or a flash memory, a hard disk, an optical disk, or the like and stores a computer program to be executed by the processing circuitry 35. The memory 32 also stores a learned model, target object information, and three-dimensional space data representing a virtual three-dimensional space representing a space in the examination room R. The learned model, the target object information, and the three-dimensional space data will be described later. The memory 32 is an exemplary storage unit in the present embodiment. The memory 32 may be achieved by a cloud.

The input interface 33 receives various input operations from the operator, converts the received input operations into electric signals, and outputs the electric signals to the processing circuitry 35. The display 34 is a liquid crystal display, a CRT display, or the like and displays various kinds of information.

The processing circuitry 35 is a processor configured to achieve a function corresponding to each computer program by reading the computer program from the memory 32 and executing the computer program. The processing circuitry 35 has an acquisition function 351, a first calculation function 352, a recognition function 353, a first specification function 354, a second calculation function 355, a second specification function 356, a third specification function 357, and a transmission function 358. The acquisition function 351 is an exemplary acquisition unit. The first calculation function 352 is an exemplary first calculation unit. The recognition function 353 is an exemplary recognition unit. The first specification function 354 is an exemplary first specification unit. The second calculation function 355 is an exemplary second calculation unit. The first calculation function 352 and the second calculation function 355 may be collectively an exemplary calculation unit. The second specification function 356 is an exemplary second specification unit. The third specification function 357 is an exemplary third specification unit. The transmission function 358 is an exemplary transmission unit.

For example, the acquisition function 351, the first calculation function 352, the recognition function 353, the first specification function 354, the second calculation function 355, the second specification function 356, the third specification function 357, and the transmission function 358, which are components of the processing circuitry 35, are stored in the memory 32 as computer-executable programs. The processing circuitry 35 reads each computer program from the memory 32 and executes the read computer program to achieve a function corresponding to the computer program. In other words, the processing circuitry 35 having read each computer program has the corresponding function illustrated in the processing circuitry 35 in FIG. 2. In FIG. 2, one processing circuitry 35 achieves processing functions of the acquisition function 351, the first calculation function 352, the recognition function 353, the first specification function 354, the second calculation function 355, the second specification function 356, the third specification function 357, and the transmission function 358, but the processing circuitry 35 may be achieved by combining a plurality of independent processors so that each processor achieves the corresponding processing function by executing the corresponding computer program.

A "processor" used in the above description means, for example, a central processing unit (CPU), a graphics processing unit (GPU), or a circuit such as an application specific integrated circuit (ASIC) or a programmable logic device (for example, a simple programmable logic device (SPLD) or a complex programmable logic device (CPLD), or a field programmable gate array (FPGA)). Each computer program may be directly incorporated in a circuit of the processor instead of being stored in the memory 140 or the memory 32. In this case, the processor achieves a function by reading and executing the computer program incorporated in the circuit.

The acquisition function 351 acquires a plurality of examination room images having parallax therebetween from the stereo camera 20 through the network interface 31. The acquisition function 351 sends the acquired examination room images to the first calculation function 352, the recognition function 353, and the third specification function 357.

The first calculation function 352 calculates depth information through image processing of two examination room images having parallax therebetween and acquired by the acquisition function 351. The depth information is the distance between an object depicted in the examination room images and the stereo camera 20. The first calculation function 352 sends the calculated depth information to the recognition function 353.

The recognition function 353 recognizes a non-evasive target body in each examination room image through image processing. The non-evasive target body is a body other than any target object and is, for example, a poster or a calendar fixed to the wall of the examination room. The non-evasive target body may be predetermined and stored in the memory 32. The recognition function 353 deletes a recognized non-evasive target body from the examination room image.

The recognition function 353 recognizes a non-evasive target body with an image recognition model by deep learning (hierarchical learning) such as R-CNN (Regions with CNN Features). The recognition function 353 may use any other image recognition method such as pattern recognition.

The recognition function 353 recognizes an image region outside the operation range of the movement mechanisms in each examination room image using the depth information calculated by the first calculation function 352. For example, the operation range of the movement mechanisms may be stored in the memory 32 in advance or acquired from the X-ray diagnostic apparatus 10. The recognition function 353 determines, as a non-evasive target image region, the image region outside the operation range of the movement mechanisms in the examination room image using a result of the recognition. In the present embodiment, the image processing provided on the examination room image by the recognition function 353 is exemplary, and the recognition function 353 may provide any other image processing such as correction on the examination room image.

The recognition function 353 sends the examination room image from which any non-evasive target body is deleted and that is provided with information indicating any non-evasive target image region or other image processing to the first specification function 354. The information indicating any non-evasive target image region is, for example, coordinate information indicating any non-evasive target image region in the examination room image.

The first specification function 354 specifies identification information of a target object depicted in the examination room image, and a region in which the target object is depicted in the examination room image, using the examination room image provided with image processing by the recognition function 353 and a learned model. The specification of identification information of the target object depicted in the examination room image by the first specification function 354 is also referred to as target object recognition, target object determination, or target object detection. In the present embodiment, the first specification function 354 excludes, as a target of the target object recognition processing, a range determined as a non-evasive target image region by the recognition function 353.

The first specification function 354 may use, for the target object recognition processing, one of the two examination room images having parallax therebetween and acquired by the acquisition function 351, or may use both images when performing the target object recognition processing.

A learned model indicates the association relation among an examination room image, identification information of a target object depicted in the examination room image, and a region in which the target object is depicted in the examination room image. The learned model is an exemplary model in the present embodiment. The learned model may be referred to as first association information.

Figure 3:
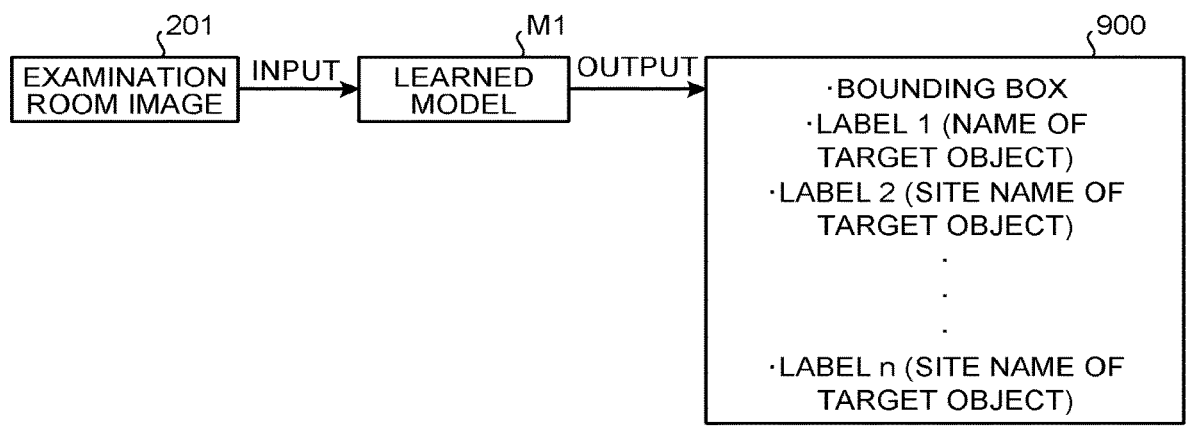
FIG. 3 is a diagram illustrating an exemplary learned model according to the first embodiment.

FIG. 3 is a diagram illustrating an exemplary learned model M1 according to the present embodiment. In the learned model M1, an examination room image 201, a bounding box indicating a region in which a target object is depicted in the examination room image 201, and labels indicating the names of the target object depicted in the examination room image 201 and a site of the target object are associated with one another. As illustrated in FIG. 3, when having received the examination room image 201 as input data, the learned model M1 outputs, as output data 900, a bounding box indicating a region in which a target object is depicted in the examination room image 201 and labels indicating the names of the target object and a site of the target object.

The name of the target object is exemplary identification information of the target object in the present embodiment. The learned model M1 may be associated with the ID of the target object or the like as the identification information of the target object. The learned model M1 of the present embodiment is also referred to as a first learned model.

Figure 4:
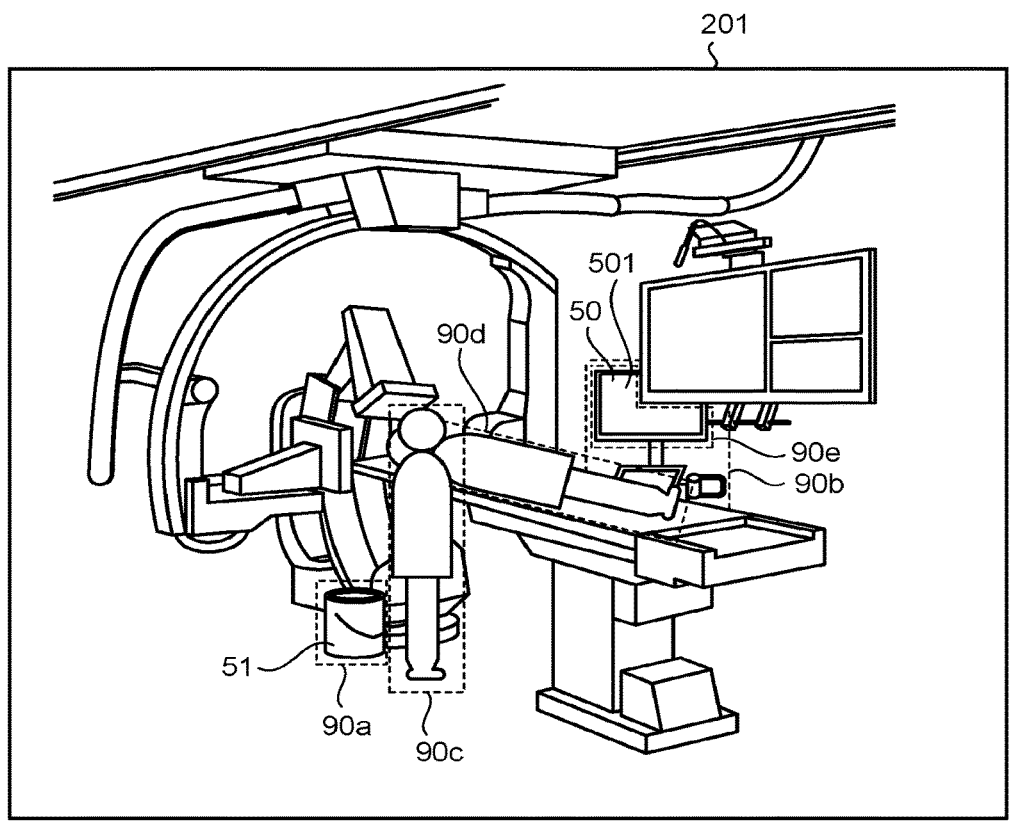
FIG. 4 is a diagram illustrating an exemplary bounding box according to the first embodiment.

FIG. 4 is a diagram illustrating exemplary bounding boxes 90a to 90e according to the present embodiment. Hereinafter, the bounding boxes 90a to 90e are simply referred to as a bounding box 90 when not distinguished from each other.

In the example illustrated in FIG. 4, target objects depicted in an examination room image 201 are the bucket 51, the ultrasonic wave diagnostic apparatus 50, the operator P2, and the subject P1. The bounding box 90a indicates a region in which the bucket 51 is depicted in the examination room image 201. The bounding box 90b indicates a region in which the ultrasonic wave diagnostic apparatus 50 is depicted in the examination room image 201. The bounding box 90c indicates a region in which the operator P2 is depicted in the examination room image 201. The bounding box 90d indicates a region in which the subject P1 is depicted in the examination room image 201.

The learned model M1 may output a bounding box 90 indicating a region in which a site of each target object is depicted in addition to the entire target object. In the example illustrated in FIG. 4, the bounding box 90e indicates a region in which a display 501 of the ultrasonic wave diagnostic apparatus 50 is depicted. The display 501 of the ultrasonic wave diagnostic apparatus 50 is an exemplary site of a target object.

In the present embodiment, the learned model M1 is constituted by a neural network and learned parameter data.

The learned model M1 is, for example, an image recognition model generated by deep learning (hierarchical learning) such as R-CNN. The learned model M1 may be generated by any other deep learning method. The deep learning method may be a multi-layer neural network such as a convolutional neural network (CNN) or a convolutional deep belief neural network (CDBN). The learned model M1 may be generated by another machine learning method such as a support vector machine (SVM).

In the present embodiment, the learned model M1 is generated by another information processing apparatus outside the medical information processing system S and stored in the memory 32 of the medical information processing apparatus 30.

In target object recognition using the learned model M1, not the entire outer shape of a target object needs to be depicted in the examination room image 201. For example, the first specification function 354 specifies a bounding box indicating the position of any target object depicted in the examination room image 201, the name of the target object, and the name of any site of the target object with the learned model M1 using the shape, color, or the like of part of the outer shape of the target object.

The first specification function 354 sends the bounding box indicating the position of the target object, the name of the target object, and the name of the site of the target object to the second calculation function 355, the second specification function 356, and the third specification function 357. In addition, the first specification function 354 determines whether any target object, the name of which cannot be specified exists in the examination room image 201, and sends a result of the determination to the second calculation function 355 and the third specification function 357.

Referring back to FIG. 2, using two examination room images having parallax therebetween and acquired by the acquisition function 351 and a target object specified by the first specification function 354, the second calculation function 355 calculates the depth information of the target object, in other words, the distance between the target object and the stereo camera 20. Although the first calculation function 352 described above calculates, for the entire range of the examination room image, the depth information of the target object depicted in the examination room image, the second calculation function 355 limits a depth information calculation target to the target object specified by the first specification function 354 and calculates more highly accurate depth information. The second calculation function 355 sends the calculated depth information of each target object to the third specification function 357.

The second specification function 356 specifies the three-dimensional shape data of the target object, one or a plurality of evasive regions of the target object, and an evasive action in each of the one or plurality of evasive regions using the name of the target object and target object information.

Figures 5, 6:
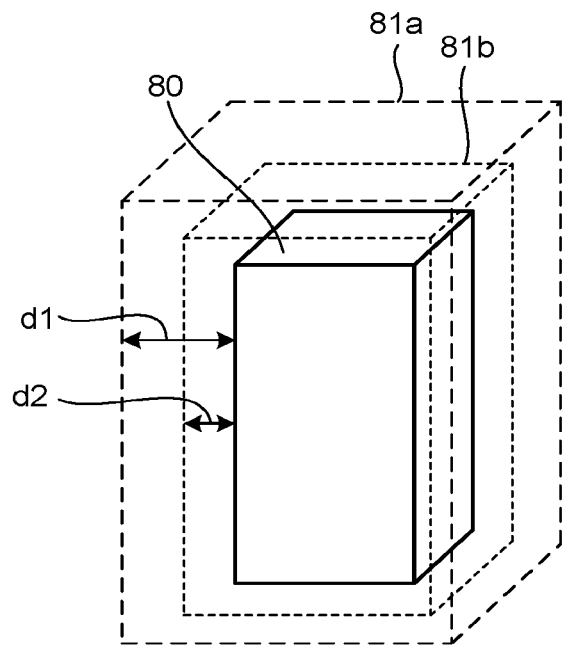
FIG. 5 is a diagram illustrating exemplary target object information according to the first embodiment.
FIG. 6 is a diagram illustrating exemplary three-dimensional shape data and an exemplary evasive region according to the first embodiment.

FIG. 5 is a diagram illustrating exemplary target object information 3201 according to the present embodiment. The target object information 3201 indicates the association relation between the identification information of the target object and the three-dimensional shape data representing the outer shape of the target object, and is exemplary association information in the present embodiment. The target object information 3201 may be referred to as second association information when the learned model M1 is referred to as the first association information.

In the present embodiment, as illustrated in FIG. 5, the names of a plurality of target objects, the three-dimensional shape data of each target object, one or a plurality of evasive regions of each target object, and an evasive action in each of the one or plurality of evasive regions are associated with one another in the target object information 3201. The name of a target object is exemplary identification information of the target object, and the ID of the target object or the like may be used in place of the name. In the target object information 3201, pieces of identification information of a plurality of target objects are associated in one-to-one relation with a plurality of pieces of three-dimensional shape data representing the outer shapes of the respective target objects.

The three-dimensional shape data is information indicating the outer shape of a target object. The three-dimensional shape data is also referred to as a three-dimensional model or a stereoscopic model. The three-dimensional shape data is produced using, for example, designing data of a medical instrument or the like to be installed in the examination room R. The three-dimensional shape data may be produced using dimensional information manually measured by a measure or the like or using results of image capturing at a plurality of angles by a stereo camera, a 3D camera, or the like.

FIG. 6 is a diagram illustrating exemplary three-dimensional shape data 80 and evasive regions 81a and 81b according to the present embodiment. For example, when a target object is Device "A" having a square pillar shape, the three-dimensional shape data 80 of Device "A" represents the longitudinal, lateral, and thickness dimensions of Device "A".

The evasive regions 81a and 81b (hereinafter, the first evasive region 81a and the second evasive region 81b are simply referred to as an evasive region 81 when not distinguished from each other) are three-dimensional regions obtained by enlarging the outer shape of the three-dimensional shape data 80. A target object and its three-dimensional shape data 80 are associated with each other in one-to-one relation. In the target object information 3201 of the present embodiment, a plurality of evasive regions 81 having sizes different from each other are associated with one target object and its three-dimensional shape data 80.

For example, as illustrated in FIG. 6, the first evasive region 81a of Device "A" is a three-dimensional region of the three-dimensional shape data 80 of Device "A" to which Distance d1 is added. The second evasive region 81b of Device "A" is smaller than the first evasive region 81a and is a three-dimensional region of the three-dimensional shape data 80 of Device "A" to which Distance d2 is added. Distance d2 is shorter than Distance d1. The number of evasive regions 81 associated with each target object may be larger than two.

An evasive action is operation of the movement mechanisms (such as the C arms 105 and the table 104) of the X-ray diagnostic apparatus 10 to evade a target object. In the target object information 3201, different evasive actions are associated with respective evasive regions 81. An evasive region 81 and an evasive action of each target object are associated with each other in one-to-one relation. For example, in the example illustrated in FIGS. 5 and 6, an evasive action in the first evasive region 81a of Device "A" is "deceleration", and an evasive action thereof is "stop" in the second evasive region 81b. When the plurality of evasive regions 81 are provided to one target object, the corresponding evasive actions are determined so that the speeds of the movement mechanisms decrease in smaller evasive regions 81 among the plurality of evasive regions 81. In other words, the evasive actions are determined so that the speed of each movement mechanism decreases as the distance between the movement mechanism and the target object becomes shorter.

The second specification function 356 sends the three-dimensional shape data 80, the evasive region 81, and the evasive action thus specified to the third specification function 357.

Referring back to FIG. 2, the third specification function 357 specifies the position and orientation of the three-dimensional shape data 80 in the virtual three-dimensional space representing the space in the examination room R using the depth information.

For example, the third specification function 357 specifies the position and orientation of a target object in the examination room R using the depth information of the target object calculated by the second calculation function 355 and a bounding box specified by the first specification function 354 as a region in which the target object is depicted in the examination room image 201. The third specification function 357 disposes the three-dimensional shape data 80 specified by the second specification function 356 in the virtual three-dimensional space using the specified position and orientation of the target object in the examination room R. The three-dimensional space data representing the virtual three-dimensional space is stored in the memory 32.

For example, since the depth information indicates the distance between the stereo camera 20 and the target object depicted in the examination room image 201, the third specification function 357 specifies the position of the target object and the angle of a surface of the target object facing the stereo camera 20 using the depth information. The third specification function 357 specifies the position and orientation of the three-dimensional shape data 80 of the target object in accordance with the specified position and angle of the surface of the target object facing the stereo camera 20. Accordingly, the third specification function 357 reproduces, in the virtual three-dimensional space using the three-dimensional shape data 80, a surface of the target object not facing the stereo camera 20, and part of the target object outside the image capturing range of the examination room image 201.

When having determined that the target object exists in the movable range of a movement mechanism of the X-ray diagnostic apparatus 10, the third specification function 357 sends a result of specification of the position and orientation of the three-dimensional shape data 80 in the virtual three-dimensional space and the evasive region 81 and the evasive action associated with the three-dimensional shape data 80 to the transmission function 358. The position and orientation of the three-dimensional shape data 80 in the virtual three-dimensional space are expressed with, for example, three-dimensional space coordinates.

When it is determined that a target object, the name of which cannot be specified by the first specification function 354 exists in the examination room image 201, the third specification function 357 may specify the position and orientation of the target object using the depth information and dispose the target object in the virtual three-dimensional space.

The transmission function 358 transmits the position and orientation of the three-dimensional shape data 80 in the virtual three-dimensional space, which are specified by the third specification function 357 and the evasive region 81 and the evasive action associated with the three-dimensional shape data 80 to the X-ray diagnostic apparatus 10.

The following describes the process of the target object recognition processing executed by the medical information processing apparatus 30 of the present embodiment configured as described above.

Figure 7:
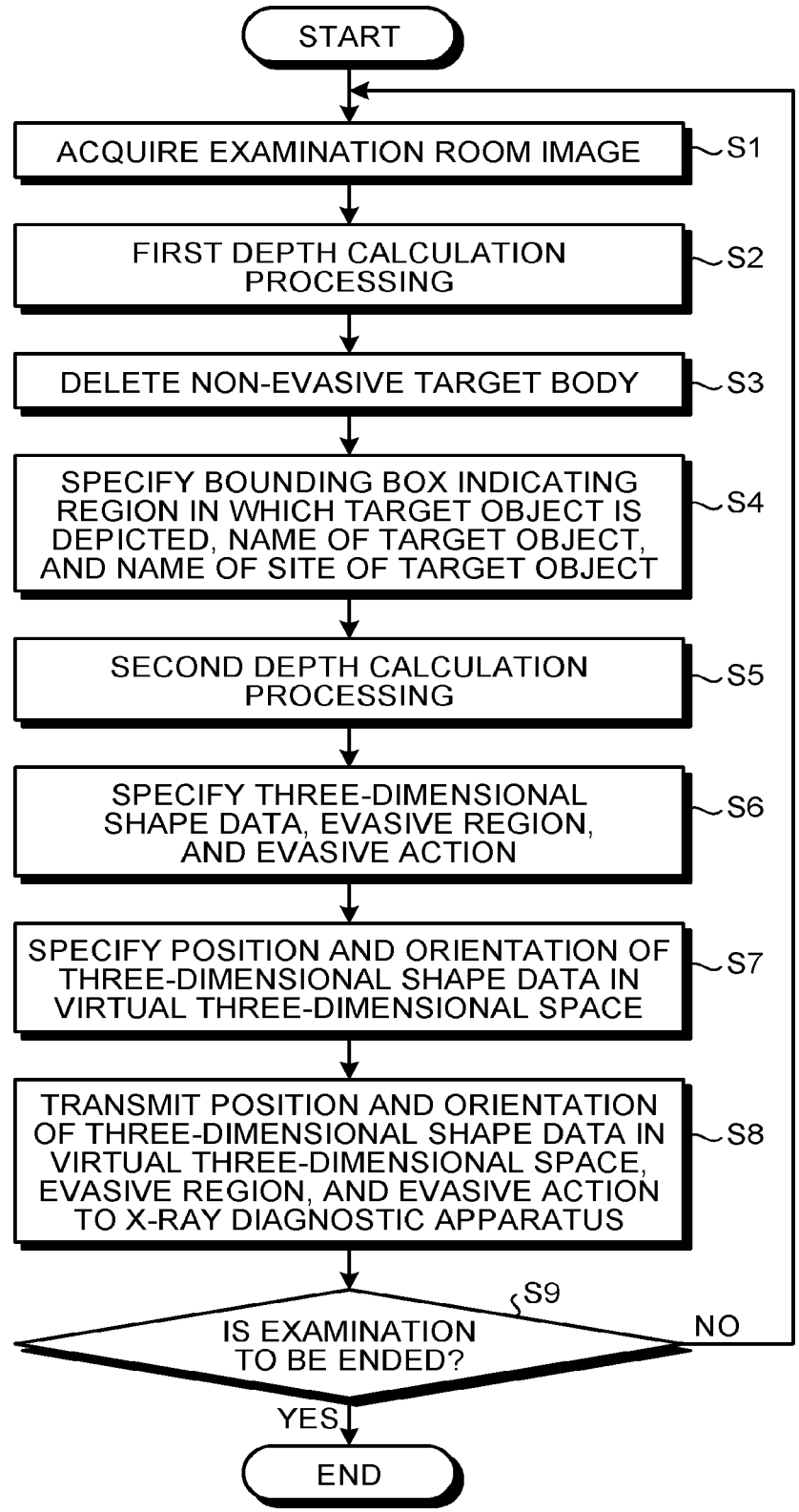
FIG. 7 is a flowchart illustrating an exemplary process of target object specification processing according to the first embodiment.

FIG. 7 is a flowchart illustrating an exemplary process of target object specification processing according to the present embodiment. The processing of the flowchart may start when inputting of a start operation by the operator P2 or the like is received or when an image-capturing start notification is received from the X-ray diagnostic apparatus 10.

First, the acquisition function 351 acquires examination room images 201 from the stereo camera 20 through the network interface 31 (S1).

Subsequently, the first calculation function 352 calculates the depth information through image processing on the two examination room images having parallax therebetween and acquired by the acquisition function 351. This processing is referred to as first depth calculation processing (S2).

Subsequently, the recognition function 353 recognizes any non-evasive target body in the examination room images through image processing and deletes the recognized non-evasive target body from the examination room images 201 (S3).

Subsequently, the first specification function 354 specifies a bounding box indicating a region in which a target object is depicted, the name of the target object, and the name of a site of the target object using the examination room images 201 provided with image processing by the recognition function 353 and the learned model M1 (S4). Specifically, the first specification function 354 inputs the examination room images 201 into the learned model M1 and obtains, as an output result, the bounding box, the name of the target object, and the name of the site of the target object.

Subsequently, using the two examination room images having parallax therebetween and acquired by the acquisition function 351 and the target object specified by the first specification function 354, the second calculation function 355 calculates the depth information of the target object. This processing is referred to as second depth calculation processing (S5).

Subsequently, the second specification function 356 specifies the three-dimensional shape data 80 of the target object, one or the plurality of evasive regions 81 of the target object, and an evasive action in each of the one or plurality of evasive regions using the name of the target object and the target object information 3201 (S6).

Subsequently, the third specification function 357 specifies the position and orientation of the three-dimensional shape data 80 in the virtual three-dimensional space using the depth information calculated by the second calculation function 355 and the bounding box specified by the first specification function 354 (S7).

Subsequently, the transmission function 358 transmits, to the X-ray diagnostic apparatus 10, the position and orientation of the three-dimensional shape data 80 in the virtual three-dimensional space, which are specified by the third specification function 357, and the evasive region 81 and the evasive action associated with the three-dimensional shape data 80 (S8).

The processing circuitry 120 of the X-ray diagnostic apparatus 10 receives information transmitted from the medical information processing apparatus 30 through the network interface 150 and controls movement of the movement mechanisms using the information transmitted from the medical information processing apparatus 30 so that the movement mechanisms evade the target object.

For example, the processing circuitry 120 of the X-ray diagnostic apparatus 10 determines the existence of the target object in the movable range of any C arm 105 or the table 104 using the information transmitted from the medical information processing apparatus 30. When having determined that the target object exists in the movable range of the C arm 105 or the table 104, the processing circuitry 120 controls operation of the C arm 105 or the table 104 so that the C arm 105 or the table 104 evades the target object.

For example, when an evasive region 81 of the three-dimensional shape data 80 of the target object exists on the movement route of a movement mechanism, the processing circuitry 120 searches for or generates an evasive route through which the movement mechanism can evade the evasive region 81 and reach a destination. In addition, the processing circuitry 120 executes control such as change of the speed of the movement mechanism or stop of the movement mechanism in accordance with an evasive action associated with the evasive region 81.

When time is needed for movement of the movement mechanism on the evasive route or when there is no evasive route on which the target object can be evaded, the processing circuitry 120 of the X-ray diagnostic apparatus 10 may cause the display 130 to display a message that suggests movement of the target object or the like.

The acquisition function 351 of the medical information processing apparatus 30 determines whether an examination end instruction is acquired from the operator through the input interface 33 (S9). When having determined that no examination end instruction is acquired from the operator ("No" at S9), the acquisition function 351 returns to the processing at S1 and continues the target object recognition processing. In the present embodiment, the target object recognition processing executed by the medical information processing apparatus 30 continues not only while the X-ray diagnostic apparatus 10 moves the C arms 105 but also until examination of the subject P1 by the X-ray diagnostic apparatus 10 ends, and when a new target object is detected or when change of the position or posture of a detected target object is detected, a result of the detection is transmitted to the X-ray diagnostic apparatus 10.

When the acquisition function 351 determines that an examination end instruction is acquired from the operator ("Yes" at S9), the processing of the flowchart ends. The examination end instruction may be transmitted from the X-ray diagnostic apparatus 10.

In this manner, the medical information processing apparatus 30 of the present embodiment specifies the identification information of the target object depicted in the examination room image 201 using the examination room image 201 acquired from the stereo camera 20 and the first association information (learned model M) indicating the association relation between the examination room image 201 and the identification information of the target object depicted in the examination room image 201, and specifies the three-dimensional shape data 80 corresponding to the specified identification information of the target object using the second association information (target object information 3201). In addition, the medical information processing apparatus 30 specifies the position of the specified three-dimensional shape data 80 using the depth information indicating the distance from the stereo camera 20 to the target object. In this manner, according to the medical information processing apparatus 30 of the present embodiment, the three-dimensional shape data 80 corresponding to the target object depicted in the examination room image 201 is specified without matching processing of the outer shape of the target object in the examination room image 201 and the three-dimensional shape data 80, and thus the stereoscopic shape of the target object can be specified fast.

For example, in a technology of a comparative example, three-dimensional shape data corresponding to a target object depicted in an examination room image is specified through shape-to-shape matching processing of the shape of the target object and three-dimensional shape data stored in advance. In such a technology, the load of processing for specifying the stereoscopic shape of the target object is large, and the processing takes time in some cases. However, according to the medical information processing apparatus 30 of the present embodiment, the stereoscopic shape of the target object in the examination room image 201 can be specified without matching processing of the outer shape of the target object and the three-dimensional shape data 80, and thus the processing time can be reduced.

The target object information 3201 of the present embodiment is information in which the identification information of a plurality of target objects, a plurality of pieces of three-dimensional shape data 80 representing the outer shapes of the respective target objects, one or the plurality of evasive regions 81 of each target object, and an evasive action in each of the one or the plurality of evasive regions 81 are associated with one another. The medical information processing apparatus 30 transmits the position and orientation of the three-dimensional shape data 80 in the virtual three-dimensional space, the one or the plurality of evasive regions 81 associated with the three-dimensional shape data 80, and an evasive action in each of the one or the plurality of evasive regions 81 to the X-ray diagnostic apparatus 10. Accordingly, the medical information processing apparatus 30 of the present embodiment can cause the X-ray diagnostic apparatus 10 to execute control of the movement mechanisms in accordance with an evasive action associated with an evasive region 81 of a specified target object.

An evasive region of the present embodiment is a three-dimensional region obtained by enlarging the outer shape of the three-dimensional shape data 80. In the target object information 3201, one piece of the three-dimensional shape data 80 is associated with a plurality of evasive regions sizes different from each other, and the evasive regions are associated with respective evasive actions different from each other. Accordingly, the medical information processing apparatus 30 of the present embodiment can cause the X-ray diagnostic apparatus 10 to execute an appropriate evasive action in accordance with the degree of proximity to a target object.

The first association information of the present embodiment is the learned model M1 in which an examination room image 201 and the identification information of the target object depicted in the examination room image 201 are associated with each other. Accordingly, the medical information processing apparatus 30 of the present embodiment can highly accurately recognize the target object depicted in the examination room image 201. For example, in a technology of matching the shape of a target object depicted in an examination room image with three-dimensional shape data stored in advance as in the above-described comparative example, when only a small range of the outer shape of the target object is captured in the examination room image, it is difficult to specify the corresponding three-dimensional shape data in some cases. In addition, it is difficult to specify the stereoscopic shape from the examination room image in some cases, depending on the image capturing angle of the target object. However, the medical information processing apparatus 30 of the present embodiment can specify the identification information of the target object with the learned model M1 using the shape, color, or the like of part of the outer shape of the target object depicted in the examination room image 201 when not the entire outer shape of the target object is depicted in the examination room image 201.

The X-ray diagnostic apparatus 10 of the present embodiment controls movement of the movement mechanisms using the position of the three-dimensional shape data 80 representing a target object in the virtual three-dimensional space, which is transmitted from the medical information processing apparatus 30, so that the movement mechanisms evade the target object that exists in the examination room R. Accordingly, the X-ray diagnostic apparatus 10 of the present embodiment can highly accurately evade the target object.

In the present embodiment, the X-ray diagnostic apparatus 10 is an exemplary medical imaging apparatus capable of capturing an image of the subject P1, but the medical imaging apparatus is not limited thereto. The medical imaging apparatus may be, for example, an X-ray computed tomography (CT) apparatus, a magnetic resonance imaging (MRI) apparatus, or a system as an integration of the X-ray diagnostic apparatus 10 and the X-ray CT apparatus.

In the present embodiment, the stereo camera 20 is an exemplary examination-room image capturing device, but the examination-room image capturing device is not limited thereto. For example, the examination-room image capturing device may be a sensor or camera capable of measuring the distance to a target object by a time-of-flight (ToF) scheme, a pattern irradiation scheme, a light-section scheme, or the like. Alternatively, the examination-room image capturing device may be a 3D camera (depth camera) capable of measuring the distance to a target object by any other well-known technology. Examination room images captured by various examination-room image capturing devices may be still images or moving images.

When the examination-room image capturing device is a 3D camera or the like configured to capture an image of the inside of the examination room R and acquire depth information, the acquisition function 351 acquires an examination room image and the depth information from the examination-room image capturing device. When this configuration is employed, the depth information does not need to be calculated in the processing circuitry 35, and thus the processing circuitry 35 does not need to include the first calculation function 352 and the second calculation function 355.

In addition, when this configuration is employed, since the 3D camera detects the depth for each pixel, the third specification function 357 collates the depth information acquired from the 3D camera with a bounding box specified by the first specification function 354 as a region in which a target object is depicted in the examination room image 201, and specifies the depth for each pixel in the region in which the target object is depicted in the examination room image 201. Then, the third specification function 357 specifies the position and orientation of the target object in the examination room R using the specified depth of each pixel.

In the present embodiment, the first specification function 354 specifies the name and bounding box 90 of a target object using the examination room image 201 and the learned model M1, but the first specification function 354 may additionally use the depth information to specify the name of the target object and the bounding box 90. In this case, the learned model M1 may indicate the association relation among the examination room image, the depth information, the identification information of the target object depicted in the examination room image, and a region in which the target object is depicted in the examination room image. Specifically, the learned model M1 may be obtained by learning the three-dimensional shape of the target object using inputting of not only the examination room image, the name of the target object, and the bounding box 90 but also the depth information, the identification information of the target object depicted in the examination room image, information indicating the region in which the target object is depicted in the examination room image, and the like.

In the present embodiment, the learned model M1 is stored in the memory 32, but among the neural network and the learned parameter data included in the learned model M1, only the learned parameter data may be stored in the memory 32. In this case, the first specification function 354 includes the neural network of the learned model M1.

The learned model M1 may include a "self-learning model" that updates an internal algorithm of the learned model M1 by acquiring feedback from the operator P2 or the like to a result of specification of a target object in an examination room image.

In the present embodiment, the learned model M1 is exemplary first association information, but the first association information may be information indicating at least the association relation between an examination room image and the identification information of the target object depicted in the examination room image, and thus is not limited to the learned model M1. The first association information may be, for example, a mathematical formula model, a look-up table, or a database. In other words, the first specification function 354 may specify the identification information of the target object with a method other than machine learning. Alternatively, the first specification function 354 may specify the identification information of the target object with, for example, well-known pattern matching or any other image recognition method. When an image recognition method is employed, the recognition function 353 and the first specification function 354 may be integrated.

In the present embodiment, the first specification function 354 performs specification processing using an examination room image provided with image processing by the recognition function 353, but the first specification function 354 may perform specification processing using an examination room image acquired by the acquisition function 351.

In the present embodiment, when a target object exists in the movable range of any movement mechanism of the X-ray diagnostic apparatus 10, the medical information processing apparatus 30 transmits a result of specification of the position and orientation of the three-dimensional shape data 80 in the virtual three-dimensional space, an evasive region 81, and an evasive action to the X-ray diagnostic apparatus 10, but these pieces of information may be transmitted to the X-ray diagnostic apparatus 10 irrespective of the existence of a target object in the movable range.

In the present embodiment, the X-ray diagnostic apparatus 10 is an exemplary medical diagnostic apparatus, but the medical diagnostic apparatus may be the entire medical information processing system S. In this case, the X-ray diagnostic apparatus 10 may be an exemplary image capturing apparatus.

Second Embodiment

In a second embodiment, the medical information processing apparatus 30 further recognizes a movable site of a target object depicted in an examination room image 201 and changes evasive regions in accordance with a result of the recognition.

The entire configuration of the medical information processing system S of the present embodiment is same as that of the first embodiment. The configurations of the X-ray diagnostic apparatus 10, the stereo camera 20, and the medical information processing apparatus 30 of the present embodiment are same as those of the first embodiment.

Similarly to the first embodiment, the processing circuitry 35 of the medical information processing apparatus 30 of the present embodiment has the acquisition function 351, the first calculation function 352, the recognition function 353, the first specification function 354, the second calculation function 355, the second specification function 356, the third specification function 357, and the transmission function 358. The acquisition function 351, the first calculation function 352, the first specification function 354, the second calculation function 355, the third specification function 357, and the transmission function 358 have functions same as those in the first embodiment.

The recognition function 353 of the present embodiment has a function same as that in the first embodiment and recognizes a movable site of a target object depicted in an examination room image. The movable site is a site at which deformation such as bending, rotation, or expansion and contraction is possible, and is, for example, a joint of an arm. The movable site may be configured to automatically deform by a mechanism such as a motor or may be manually deformed by the operator P2 or the like.

Figure 8:
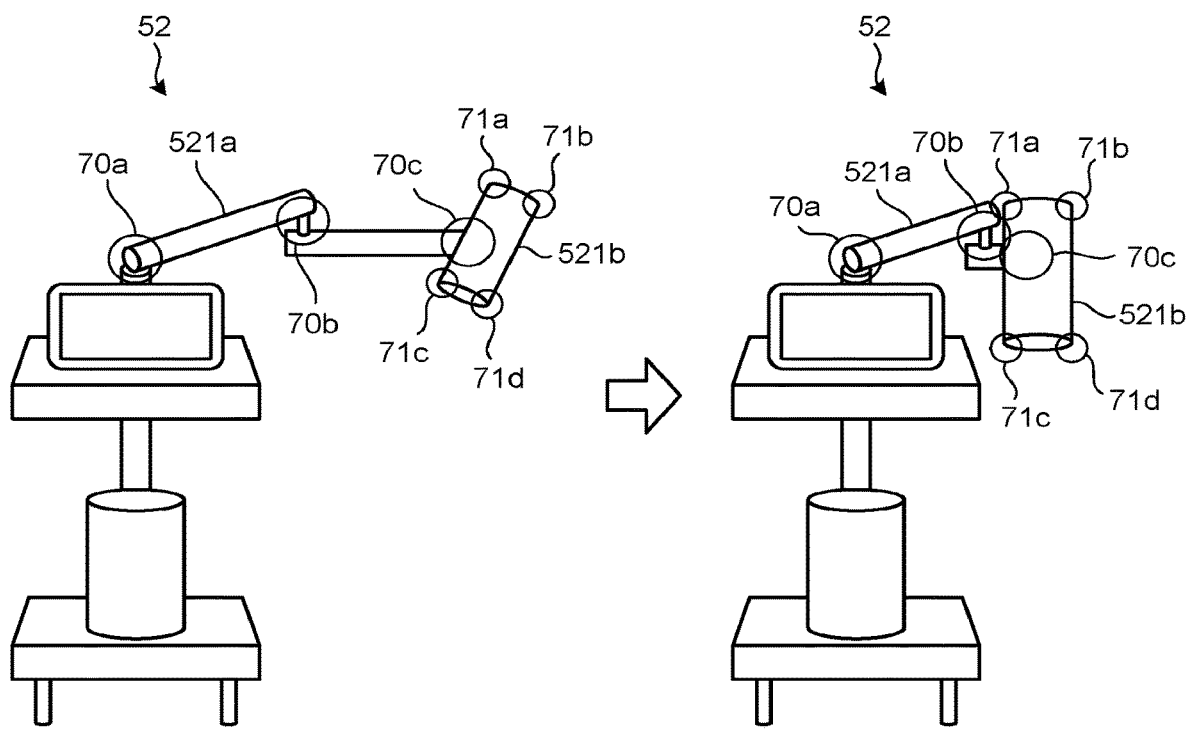
FIG. 8 is a diagram illustrating an exemplary target object including a movable site according to a second embodiment.

FIG. 8 is a diagram illustrating an exemplary target object including movable sites 70a to 70c according to the present embodiment. FIG. 8 illustrates an injector 52 as an exemplary target object. The injector 52 includes a movable arm 521a, and a head 521b attached to a leading end of the arm 521a.

The movable arm 521a includes the movable sites 70a to 70c. Hereinafter, the movable sites 70a to 70c are simply referred to as a movable site 70 when not distinguished from each other. For example, as the movable site 70 deforms, the shape of the injector 52 changes from the state illustrated on the left side in FIG. 8 to the state illustrated on the right side in FIG. 8. The shape of the injector 52 also changes from the state illustrated on the right side in FIG. 8 to the state illustrated on the left side in FIG. 8.

The recognition function 353 recognizes the movable site 70 using an examination room image 201 by an image recognition method such as pattern recognition.

The recognition function 353 also recognizes end parts 71a to 71d of the target object from the examination room image 201 by an image recognition method such as edge detection. Hereinafter, the end parts 71a to 71d are simply referred to as an end part 71 when not distinguished from each other. In FIG. 8, the recognition function 353 only recognizes the end part 71 of the head 521b, the position of which is variable, but may also recognize an end part 71 of another site. The method of recognition of the movable site 70 and the method of recognition of the end part 71 are not limited to the above-described examples but a method such as deep learning may be employed.

The recognition function 353 sends a result of the recognition of the movable site 70 and the end part 71 to the second specification function 356.

The second specification function 356 of the present embodiment has a function the same as that in the first embodiment and extends a place near the movable site 70 in the one or the plurality of evasive regions 81 associated with the three-dimensional shape data 80 specified from the target object information 3201.

Figure 9:
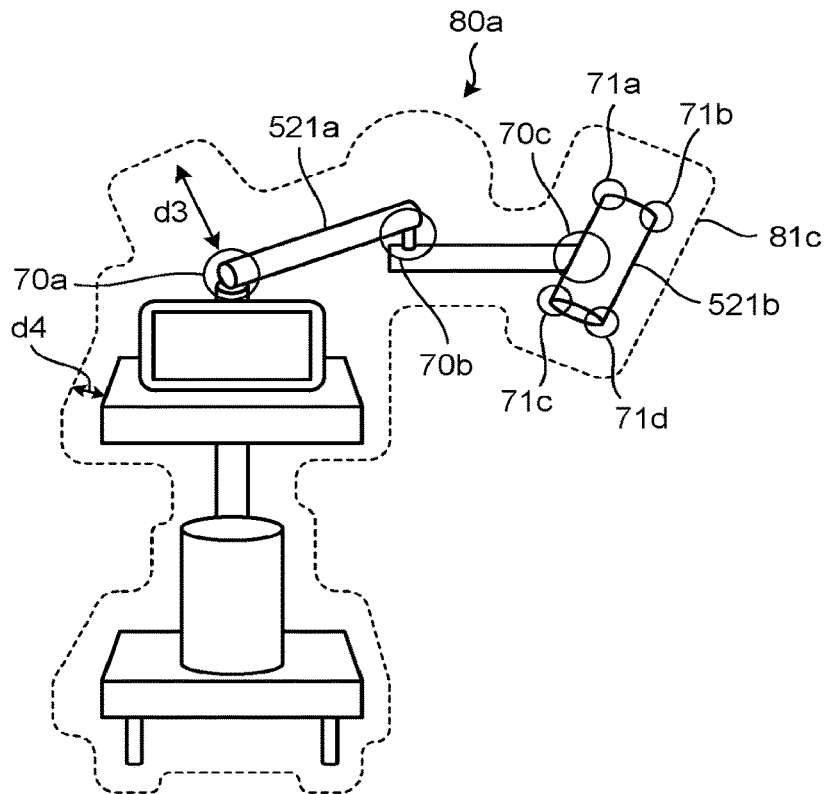
FIG. 9 is a diagram illustrating an exemplary evasive region 81 after extension according to the second embodiment.

FIG. 9 is a diagram illustrating an exemplary evasive region 81 after the extension according to the present embodiment. In the example illustrated in FIG. 9, the second specification function 356 extends a place near the movable site 70 in an evasive region 81c of a three-dimensional shape data 80a of the injector 52. Distance d4 illustrated in FIG. 9 is the distance between the three-dimensional shape data 80a and the outer periphery of the evasive region 81c in the evasive region 81 before the extension. Near the movable site 70, the second specification function 356 extends the distance between the three-dimensional shape data 80a and the outer periphery of the evasive region 81c to Distance d3, which is longer than Distance d4.

The second specification function 356 may extend the evasive region 81c near the entire arm 521a including the movable site 70.

In this manner, the medical information processing apparatus 30 of the present embodiment recognizes the movable site 70 of the target object depicted in the examination room image 201 and extends a place near the movable site 70 in the one or the plurality of evasive regions 81 associated with the three-dimensional shape data 80 of the target object. Accordingly, the medical information processing apparatus 30 of the present embodiment has the effect of the first embodiment and can ensure the evasive regions 81 when the shape of the target object deforms.

The second specification function 356 of the present embodiment may deform three-dimensional shape data 80 stored in the memory 32 in accordance with the shape of the target object depicted in the examination room image 201 using a result of the recognition of the movable site 70 and the end part 71. In this case, when no three-dimensional shape data 80 is prepared in advance for a deformation pattern, change of the shape of the target object can be reflected onto the three-dimensional shape data 80, and thus the number of patterns of three-dimensional shape data 80 stored in advance can be reduced.

Third Embodiment

In a third embodiment, the medical information processing apparatus 30 detects a target object using an examination protocol when not the entire target object is depicted in an examination room image 201.

The entire configuration of the medical information processing system S of the present embodiment is same as that of the first embodiment. The configurations of the X-ray diagnostic apparatus 10, the stereo camera 20, and the medical information processing apparatus 30 of the present embodiment are same as those of the first embodiment.

The memory 32 of the medical information processing apparatus 30 of the present embodiment stores a second learned model in addition to contents same as those of the first embodiment. The second learned model will be described later in detail.

Similarly to the first embodiment, the processing circuitry 35 of the medical information processing apparatus 30 of the present embodiment has the acquisition function 351, the first calculation function 352, the recognition function 353, the first specification function 354, the second calculation function 355, the second specification function 356, the third specification function 357, and the transmission function 358. The acquisition function 351, the first calculation function 352, the recognition function 353, the second calculation function 355, the second specification function 356, the third specification function 357, and the transmission function 358 have functions same as those in the first embodiment.

The first specification function 354 of the present embodiment has a function same as that in the first embodiment and estimates the identification information (for example, name) and position of a target object that exists in the examination room R using an examination protocol executed by the X-ray diagnostic apparatus 10.

The examination protocol is information indicating the procedure of examination at the X-ray diagnostic apparatus 10 and defines scanning target sites and various scanning execution orders.

More specifically, the first specification function 354 of the present embodiment estimates the identification information and position of a target object that exists in the examination room R using the examination protocol executed at the X-ray diagnostic apparatus 10 and the second learned model. Then, the first specification function 354 of the present embodiment recognizes the target object in an examination room image using a result of the estimation of the identification information and the position of the target object. For example, when specifying a target object, only a part of which is captured in the examination room image or a target object hidden by another target object and not depicted in the examination room image, the first specification function 354 employs an estimation result based on the examination protocol and the second learned model, thereby improving the rate of recognition of the target object.

The second learned model is a model in which the identification information of any target object that exists in the examination room R and the position of the target object are associated with each other for each of a plurality of examination protocols.

Disposition of target objects such as a medical instrument installed in the examination room R and the operator P2 is determined for each examination protocol in some cases. The second learned model of the present embodiment is generated by learning disposition of target objects for each examination protocol.

Figure 10:
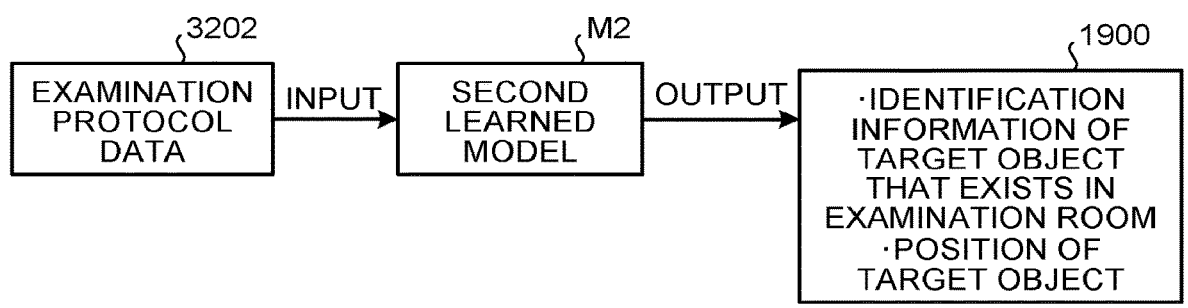
FIG. 10 is a diagram illustrating an exemplary second learned model according to a third embodiment.

FIG. 10 is a diagram illustrating an exemplary second learned model M2 according to the present embodiment. As illustrated in FIG. 10, when having received examination protocol data 3202 as input data, the second learned model M2 outputs output data 1900. The output data 1900 includes the identification information of the target object that exists in the examination room R and the position of the target object.

For example, the examination protocol executed at the X-ray diagnostic apparatus 10 may be acquired from the X-ray diagnostic apparatus 10 through the network interface 31 by the acquisition function 351 or may be input by the operator P2 through the input interface 33.

Accordingly, the medical information processing apparatus 30 of the present embodiment has the effect of the first embodiment and estimates the identification information of the target object that exists in the examination room R and the position of the target object using the examination protocol executed at the X-ray diagnostic apparatus 10, thereby improving the rate of recognition of the target object.

In the present embodiment, the second learned model M2 is separated from the learned model M1, but may be integrated with the learned model M1.

Disposition of a medical instrument, the operator P2, or the like in the examination room R is determined in some cases, depending on the operator P2 who operates the X-ray diagnostic apparatus 10. Thus, the first specification function 354 may estimate the identification information and position of a target object in the examination room R on the basis of identification information of the operator P2 of the X-ray diagnostic apparatus 10.

For example, the second learned model M2 may be a model in which the identification information of the target object that exists in the examination room R and the position of the target object are associated with each other for each of a plurality of operators P2.

When this configuration is employed, for example, identification information with which an operator P2 who operates the X-ray diagnostic apparatus 10 can be specified is input by the operator P2 through the input interface 33.

When this configuration is employed, the medical information processing apparatus 30 of the present embodiment estimates the identification information of the target object that exists in the examination room R and the position of the target object on the basis of the identification information of the operator P2 who operates the X-ray diagnostic apparatus 10, thereby also improving the rate of recognition of the target object.

Fourth Embodiment

In the above-described first to third embodiments, the first learned model M1 or the second learned model M2 is generated by another information processing apparatus outside the medical information processing system S and stored in the memory 32 of the medical information processing apparatus 30, but in a fourth embodiment, the medical information processing apparatus 30 has a learning function to generate the first learned model M1 or the second learned model M2.

Figure 11:
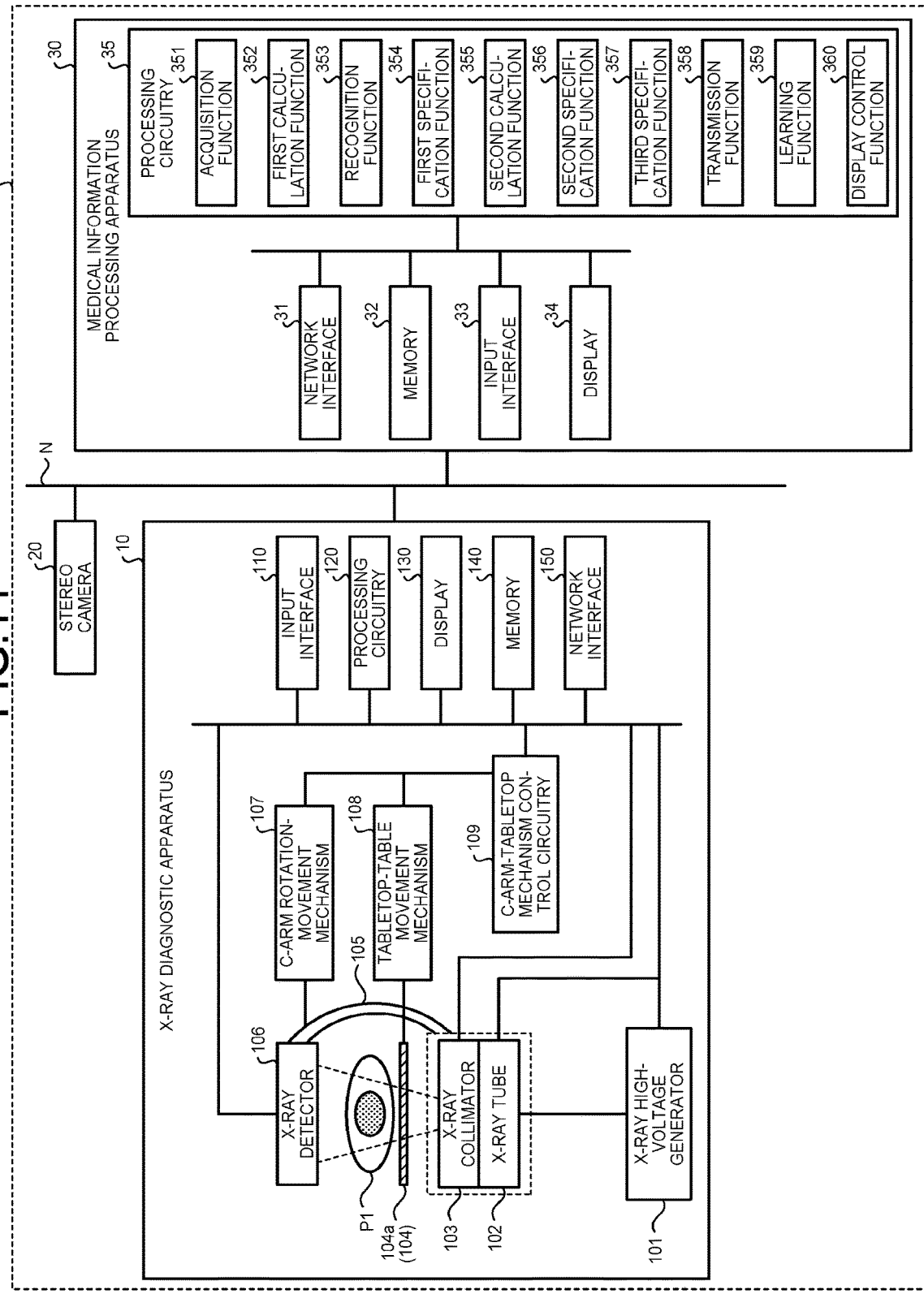
FIG. 11 is a block diagram illustrating an exemplary entire configuration of a medical information processing system according to a fourth embodiment.

FIG. 11 is a block diagram illustrating an exemplary entire configuration of the medical information processing system S according to the present embodiment. The entire configuration of the medical information processing system S of the present embodiment is same as that of the first embodiment. The configurations of the X-ray diagnostic apparatus 10 and the stereo camera 20 of the present embodiment are same as those in the first embodiment.

The processing circuitry 35 of the medical information processing apparatus 30 of the present embodiment has the acquisition function 351, the first calculation function 352, the recognition function 353, the first specification function 354, the second calculation function 355, the second specification function 356, the third specification function 357, the transmission function 358, a learning function 359, and a display control function 360. The acquisition function 351, the first calculation function 352, the recognition function 353, the first specification function 354, the second calculation function 355, the second specification function 356, the third specification function 357, and the transmission function 358 have functions same as those in the first embodiment.

Figure 12:
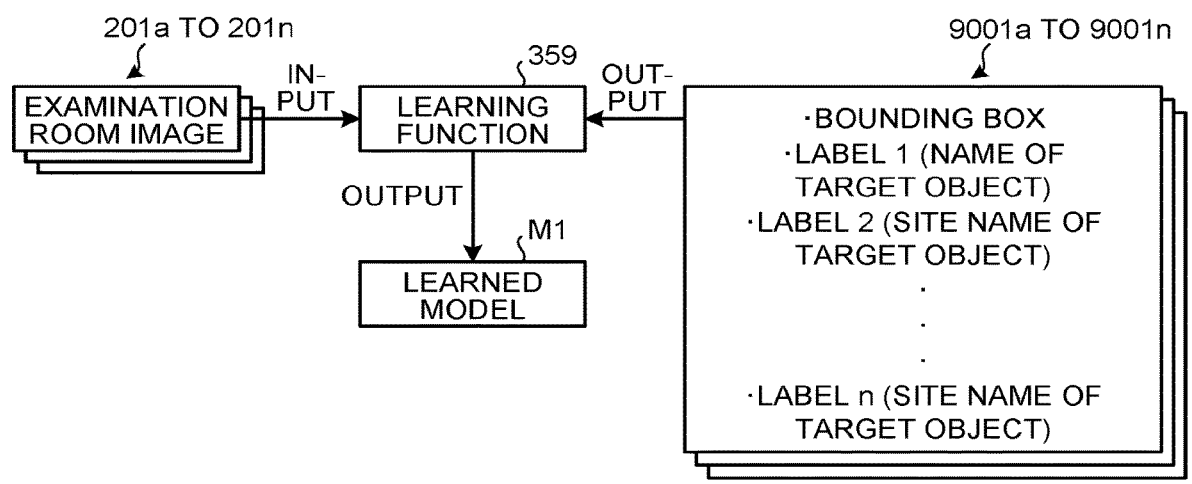
FIG. 12 is a diagram for description of learning processing according to the fourth embodiment.

FIG. 12 is a diagram for description of learning processing according to the present embodiment.

As illustrated in FIG. 12, for example, using a plurality of examination room images 201*a* to 201*n* as learning data and teacher data 9001*a* to 9001*n* corresponding to the respective examination room images 201*a* to 201*n*, the learning function 359 learns the association relation among the examination room image 201, the identification information of any target object depicted in the examination room image 201, and a region (the bounding box 90) in which the target object is depicted in the examination room image 201, thereby generating the first learned model M1. Hereinafter, the teacher data 9001*a* to 9001*n* are simply referred to as teacher data 9001 when not distinguished from each other.

The teacher data 9001 is, for example, the identification information (for example, name) of a target object depicted in the examination room image 201, and a region (the bounding box 90) in which the target object is depicted in the examination room image 201. For example, the teacher data 9001 may be acquired from the outside through the network interface 31. When the examination room image 201 is displayed on the display 34 by the display control function 360 to be described later, the teacher data 9001 corresponding to the displayed examination room image 201 may be input by the operator P2 through the input interface 33.

The examination room image 201 is, for example, an examination room image in which the X-ray diagnostic apparatus 10 at rest or in operation is depicted.

The learning function 359 may use, as learning data, a picture of the X-ray diagnostic apparatus 10, a 3D graphics image of the X-ray diagnostic apparatus 10, a picture of a medical instrument used in the examination room R, a 3D graphics image of the medical instrument used in the examination room R, a 3D graphics image including the X-ray diagnostic apparatus 10 and the medical instrument used in the examination room R, or the like.

As described in the first embodiment, the learning method may be a deep learning method of a multi-layer neural network such as a R-CNN, a convolutional neural network (CNN), a convolutional deep belief neural network (CDBN), or another machine learning method such as a support vector machine (SVM).

The learning function 359 may additionally generate the second learned model M2. In this case, the learning data is the identification information of the examination protocol data 3202 or the operator P2. The teacher data 9001 is the position and orientation of the three-dimensional shape data 80 of a target object in the virtual three-dimensional space and the identification information of the target object.

The learning function 359 may generate the second learned model M2 by learning, using the learning data and the teacher data 9001, the association relation among the identification information of the examination protocol data 3202 or the operator P2, the position and orientation of the three-dimensional shape data 80 of a target object in the virtual three-dimensional space, and the identification information of the target object.

Referring back to FIG. 11, the display control function 360 causes the display 34 to display the examination room image 201 as learning data.

The medical information processing apparatus 30 of the present embodiment has the effect of the first embodiment and can swiftly generate or update the first learned model M1 or the second learned model M2 when, for example, a medical instrument used in the examination room R or an examination protocol is newly added, since the first learned model M1 or the second learned model M2 is generated in the medical information processing apparatus 30.

First Modification

In each above-described embodiment, the medical information processing apparatus 30 specifies the position and orientation of the three-dimensional shape data 80 of a target object using a latest examination room image 201, but the medical information processing apparatus 30 may specify the position and orientation of the three-dimensional shape data 80 of a target object in the virtual three-dimensional space using a position at which the target object is recognized in the past.

For example, as a movement mechanism of the X-ray diagnostic apparatus 10 or a medical instrument in the examination room R moves, a target object becomes hidden and cannot be captured by the stereo camera 20 in some cases. In such a case, for example, the medical information processing apparatus 30 of the present modification may store a position at which the target object is detected last, and transmit an assumed position and orientation of the three-dimensional shape data 80 of the target object to the X-ray diagnostic apparatus 10 under the premise that another object may exist at the position. Alternatively, the X-ray diagnostic apparatus 10 may store a position at which the target object is detected last and control the movement mechanisms under the premise that another object may exist at the position.

The first specification function 354 of the medical information processing apparatus 30 may recognize a target object moving inside the examination room R using a plurality of examination room images 201 captured in a temporally sequential manner. For example, the first specification function 354 may use a result of recognition of the target object in each examination room image 201 for the target object recognition processing of the subsequently captured examination room images 201 and trace the target object moving inside the examination room R through the examination room images 201. When this configuration is employed, the medical information processing apparatus 30 can continuously recognize the target object when the target object moves and hides behind another target object and the ratio of part of the target object, which is captured in each examination room image 201, against the entire image thereof decreases as time elapses.

Second Modification

Functions of the medical information processing apparatus 30 in each above-described embodiment may be configured as functions of the X-ray diagnostic apparatus 10. For example, the processing circuitry 120 of the X-ray diagnostic apparatus 10 may have an acquisition function, a first calculation function, a recognition function, a first specification function, a second calculation function, a second specification function, and a third specification function. When this configuration is employed, the X-ray diagnostic apparatus 10 may be an exemplary medical information processing apparatus.

Alternatively, functions of the medical information processing apparatus 30 in each above-described embodiment may be configured as functions of an examination-room image capturing device such as the stereo camera 20. For example, the stereo camera 20 may have an acquisition function, a first calculation function, a recognition function, a first specification function, a second specification function, a second calculation function, a third specification function, and a transmission function. When this configuration is employed, the acquisition function is also referred to as an image capturing function. When this configuration is employed, the examination-room image capturing device may be an exemplary medical information processing apparatus.

Third Modification

In each above-described embodiment, the three-dimensional shape data 80 of a target object is generated in advance and stored in the memory 32 or the memory 140, but a configuration in which the three-dimensional shape data 80 is generated by the processing circuitry 35 of the medical information processing apparatus 30 or the processing circuitry 120 of the X-ray diagnostic apparatus 10 may be employed.

For example, the processing circuitry 35 of the medical information processing apparatus 30 or the processing circuitry 120 of the X-ray diagnostic apparatus 10 may have a registration function to measure the outer shape of a target object using an image captured by an examination-room image capturing device and the depth information and register a result of the measurement to the memory 32 or the memory 140 as the three-dimensional shape data 80.

For example, when it is determined that a target object that cannot be specified using the learned models M1 and M2 and the target object information 3201 exists in the examination room image 201, the registration function generates the three-dimensional shape data 80 of the target object and updates the learned models M1 and M2 and the target object information 3201 using a result of the generation.

In each above-described embodiment, each evasive region 81 is associated with the name of a target object and the three-dimensional shape data 80 and stored in the memory 32 or the memory 140 in advance as described with reference to FIG. 5, but a configuration in which the evasive region 81 is calculated by the processing circuitry 35 of the medical information processing apparatus 30 or the processing circuitry 120 of the X-ray diagnostic apparatus 10 may be employed. For example, when this configuration is employed, for each of the plurality of evasive regions 81 having sizes different from each other, the distance (for example, Distance d1 and Distance d2 in FIG. 6) from the three-dimensional shape data 80 to the outer edge of the evasive region 81 is stored in the memory 32 or the memory 140 in advance. Then, the second specification function 356 may calculate an evasive region 81 using a result of recognition of a target object by the first specification function 354, the three-dimensional shape data 80, and Distances d1 and d2.

Fourth Modification

In each above-described embodiment, recognition of any evasive target object in the examination room R in which the X-ray diagnostic apparatus 10 is installed is described, but application of the present technology is not limited to the examination room R.

For example, the technology of each above-described embodiment may be applied to recognition of an evasive target object in a medical treatment room in which a radiation treatment apparatus is installed. The radiation treatment apparatus is an exemplary medical treatment apparatus in the present modification. For example, the medical information processing system S of the present modification includes the radiation treatment apparatus, the stereo camera 20, and the medical information processing apparatus 30. The medical information processing system S does not need to include the stereo camera 20.

Specifically, the radiation treatment apparatus includes a medical treatment device configured to perform medical treatment of the subject P1. The medical treatment device includes, for example, a mount including a radiation generator and a radiation limiter, and a table device including a tabletop on which the subject P1 can be placed. The medical treatment device also includes a movement mechanism. In this case, the mount and the tabletop are exemplary movement mechanisms. The radiation treatment apparatus is not limited to this configuration. The radiation treatment apparatus includes a controller configured to control the movement mechanisms using the position of three-dimensional shape data.

For processing to evade a target object, the radiation treatment apparatus of the present modification may have functions same as those of the X-ray diagnostic apparatus 10 in each above-described embodiment.

The medical information processing apparatus 30 of the present modification may have functions same as those in each above-described embodiment.

The radiation treatment apparatus may have functions of the medical information processing apparatus 30 in each above-described embodiment. In this case, the radiation treatment apparatus may be an exemplary medical information processing apparatus. The entire medical information processing system S may be a medical treatment apparatus. In this case, the radiation treatment apparatus may be an exemplary medical treatment device.

According to at least one of the above-described embodiments, it is possible to highly accurately recognize the position and orientation of an evasive target object that exists in an examination room or a medical treatment room.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus comprising a processor configured to:

acquire an examination room image obtained by capturing an inside of an examination room in which a medical imaging apparatus including a movement mechanism is installed, specify identification information of a target object depicted in the examination room image using the examination room image, specify three-dimensional shape data corresponding to the identification information of the target object using the identification information of the target object, and specify a position of the three-dimensional shape data in a virtual three-dimensional space representing a space in the examination room using depth information indicating distance from an examination-room image capturing device having captured the examination room image to the target object depicted in the examination room image.

2. The medical information processing apparatus according to claim 1, wherein the processor is configured to:
specify the three-dimensional shape data corresponding to the identification information of the target object using the identification information of the target object and association information, and transmit the position and orientation of the three-dimensional shape data in the virtual three-dimensional space, one or a plurality of evasive regions associated with the three-dimensional shape data, and an evasive action in each of the one or the plurality of evasive regions to the medical imaging apparatus, and the association information is information in which identification information of a plurality of target objects, a plurality of pieces of three-dimensional shape data representing outer shapes of the respective target objects, one or a plurality of evasive regions of each target object, and an evasive action in each of the one or the plurality of evasive regions are associated with one another.

3. The medical information processing apparatus according to claim 2, wherein the one or the plurality of evasive regions are three-dimensional regions obtained by enlarging an outer shape of the three-dimensional shape data, and in the association information, one piece of the three-dimensional shape data is associated with a plurality of evasive regions having sizes different from each other, and the evasive regions are associated with respective evasive actions different from each other.

4. The medical information processing apparatus according to claim 1, wherein the processor is configured to:
specify the identification information of the target object using a model indicating an association relation between the examination room image and the identification information of the target object depicted in the examination room image, and the model is a learned model in which the examination room image and the identification information of the target object depicted in the examination room image are associated with each other.

5. The medical information processing apparatus according to claim 2, wherein the processor is configured to:

recognize a movable site of the target object depicted in the examination room image, and extend a place near the movable site in the one or the plurality of evasive regions associated with the three-dimensional shape data of the target object.

6. The medical information processing apparatus according to claim 1, wherein the processor is configured to:

estimate identification information and a position of the target object that exists in the examination room using an examination protocol executed by the medical imaging apparatus or identification information of an operator of the medical imaging apparatus, and specify the identification information of the target object depicted in the examination room image using a result of the estimation.

7. The medical information processing apparatus according to claim 6, wherein the processor is configured to:

estimate the identification information and the position of the target object that exists in the examination room using an examination protocol executed by the medical imaging apparatus and a learned model in which the identification information and the position of the target object that exists in the examination room are associated with each other for each of a plurality of examination protocols.

8. The medical information processing apparatus according to claim 6, wherein the processor is configured to:

estimate the identification information and the position of the target object that exists in the examination room using the operator of the medical imaging apparatus and a learned model in which the identification information and the position of the target object that exists in the examination room are associated with each other for each of a plurality of operators.

9. A medical diagnostic apparatus comprising:

an image capturing apparatus including a movement mechanism and configured to capture an image of a subject; and a processor configured to:
acquire an examination room image obtained by capturing an inside of an examination room, specify identification information of a target object depicted in the examination room image using the examination room image, specify three-dimensional shape data corresponding to the identification information of the target object using the identification information of the target object, specify a position of the three-dimensional shape data in a virtual three-dimensional space representing a space in the examination room using depth information indicating distance from an examination-room image capturing device having captured the examination room image to the target object depicted in the examination room image, and control the movement mechanism using the specified position of the three-dimensional shape data.

10. A medical information processing system comprising:
a medical imaging apparatus capable of capturing an image of a subject in an examination room; and a medical information processing apparatus, wherein the medical imaging apparatus includes
a movement mechanism that is movable, and
a controller configured to control movement of the movement mechanism using a position of three-dimensional shape data representing a target object in a virtual three-dimensional space representing a space in the examination room, the medical information processing apparatus includes a processor configured to:
specify, using an examination room image captured by an examination-room image capturing device configured to capture an image of an inside of the examination room, identification information of the target object depicted in the examination room image, specify the three-dimensional shape data corresponding to the identification information of the target object using the identification information of the target object, specify the position of the three-dimensional shape data in a virtual three-dimensional space representing a space in the examination room using depth information indicating distance from the examination-room image capturing device to the target object depicted in the examination room image, and transmit the position of the three-dimensional shape data in the virtual three-dimensional space to the medical imaging apparatus.

11. A medical information processing method comprising:
acquiring an examination room image obtained by capturing an inside of an examination room in which a medical imaging apparatus including a movement mechanism is installed;
specifying identification information of a target object depicted in the examination room image using the examination room image;
specifying three-dimensional shape data corresponding to the identification information of the target object using the identification information of the target object; and
specifying a position of the three-dimensional shape data in a virtual three-dimensional space representing a space in the examination room using depth information indicating distance from an examination-room image capturing device having captured the examination room image to the target object depicted in the examination room image.

12. The medical information processing method according to claim 11, further comprising:
specifying the three-dimensional shape data corresponding to the identification information of the target object using the identification information of the target object and association information; and
transmitting the position and orientation of the three-dimensional shape data in the virtual three-dimensional space, one or a plurality of evasive regions associated with the three-dimensional shape data, and an evasive action in each of the one or the plurality of evasive regions to the medical imaging apparatus, wherein
the association information is information in which identification information of a plurality of target objects, a plurality of pieces of three-dimensional shape data representing outer shapes of the respective target objects, one or a plurality of evasive regions of each target object, and an evasive action in each of the one or the plurality of evasive regions are associated with one another.

13. The medical information processing method according to claim 12, wherein
the one or the plurality of evasive regions are three-dimensional regions obtained by enlarging an outer shape of the three-dimensional shape data, and
in the association information, one piece of the three-dimensional shape data is associated with a plurality of evasive regions having sizes different from each other, and the evasive regions are associated with respective evasive actions different from each other.

14. The medical information processing method according to claim 11, further comprising specifying the identification information of the target object using a model indicating an association relation between the examination room image and the identification information of the target object depicted in the examination room image, wherein
the model is a learned model in which the examination room image and the identification information of the target object depicted in the examination room image are associated with each other.

15. The medical information processing method according to claim 12, further comprising:
recognizing a movable site of the target object depicted in the examination room image; and
extending a place near the movable site in the one or the plurality of evasive regions associated with the three-dimensional shape data of the target object.

16. The medical information processing method according to claim 11, further comprising:
estimating identification information and a position of the target object that exists in the examination room using an examination protocol executed by the medical imaging apparatus or identification information of an operator of the medical imaging apparatus; and
specifying the identification information of the target object depicted in the examination room image using a result of the estimation.

17. The medical information processing method according to claim 16, further comprising estimating the identification information and the position of the target object that exists in the examination room using an examination protocol executed by the medical imaging apparatus and a learned model in which the identification information and the position of the target object that exists in the examination room are associated with each other for each of a plurality of examination protocols.

18. A medical imaging apparatus installed in an examination room and capable of capturing an image of a subject, the medical imaging apparatus comprising:
a movement mechanism that is movable; and
a controller configured to
acquire an examination room image obtained by capturing an inside of the examination room,
specify identification information of a target object depicted in the examination room image using the examination room image,
specify three-dimensional shape data corresponding to the identification information of the target object using the identification information of the target object,
specify a position of the three-dimensional shape data in a virtual three-dimensional space representing a space in the examination room using depth information indicating distance from an examination-room image capturing device having captured the examination room image to the target object depicted in the examination room image, and
control, using the specified position of the three-dimensional shape data, movement of the movement mechanism so that the movement mechanism evades the target object that exists in the examination room.

19. A medical treatment apparatus comprising:
a medical treatment device including a movement mechanism and configured to perform medical treatment of a subject; and
a processor configured to:
acquire a medical treatment room image obtained by capturing an inside of a medical treatment room, specify identification information of a target object depicted in the medical treatment room image using the medical treatment room image, specify three-dimensional shape data corresponding to the identification information of the target object using the identification information of the target object, specify a position of the three-dimensional shape data in a virtual three-dimensional space representing a space in the medical treatment room using depth information indicating distance from a medical treatment room image capturing device having captured the medical treatment room image to the target object depicted in the medical treatment room image, and control the movement mechanism using the specified position of the three-dimensional shape data.

20. A medical information processing apparatus comprising a processor configured to:

acquire a medical treatment room image obtained by capturing an inside of a medical treatment room in which a medical treatment apparatus including a movement mechanism is installed, specify identification information of a target object depicted in the medical treatment room image using the medical treatment room image, specify three-dimensional shape data corresponding to the identification information of the target object using the identification information of the target object, and specify a position of the three-dimensional shape data in a virtual three-dimensional space representing a space in the medical treatment room using depth information indicating distance from a medical treatment room image capturing device having captured the medical treatment room image to the target object depicted in the medical treatment room image.

* * * * *